United States Patent
Ochiai et al.

(10) Patent No.: US 11,168,800 B2
(45) Date of Patent: Nov. 9, 2021

(54) CHECK-VALVE

(71) Applicant: PIGEON CORPORATION, Tokyo (JP)

(72) Inventors: Yukifumi Ochiai, Tokyo (JP); Yuichiro Tanaka, Tokyo (JP); Yoshihito Sugiyama, Tokyo (JP)

(73) Assignee: PIGEON CORPORATION, Tokyo (JP)

(*) Notice: Subject to any disclaimer, the term of this patent is extended or adjusted under 35 U.S.C. 154(b) by 0 days.

(21) Appl. No.: 16/622,001

(22) PCT Filed: Jun. 22, 2018

(86) PCT No.: PCT/JP2018/023870
§ 371 (c)(1),
(2) Date: Dec. 12, 2019

(87) PCT Pub. No.: WO2019/004093
PCT Pub. Date: Jan. 3, 2019

(65) Prior Publication Data
US 2020/0141504 A1    May 7, 2020

(30) Foreign Application Priority Data
Jun. 30, 2017   (JP) .............................. JP2017-128898

(51) Int. Cl.
*F16K 15/03*     (2006.01)
*F16K 15/18*     (2006.01)
(Continued)

(52) U.S. Cl.
CPC ............. *F16K 15/031* (2013.01); *A61M 1/06* (2013.01); *F16K 15/145* (2013.01);
(Continued)

(58) Field of Classification Search
CPC .... F16K 15/031; F16K 15/144; F16K 15/145; Y10T 137/7888; Y10T 137/7891; A61M 1/06; A61M 1/062; A61M 1/064
See application file for complete search history.

(56) References Cited

U.S. PATENT DOCUMENTS 2,881,795 A * 4/1959 Waldenmaier ........ F16K 15/144
                                                         137/855
3,370,305 A * 2/1968 Goott ..................... A61F 2/2403
                                                         623/2.21
(Continued)

FOREIGN PATENT DOCUMENTS

| CN | 204942640 U | 1/2016 |
|---|---|---|
| EP | 1195170 A1 | 4/2002 |

(Continued)

OTHER PUBLICATIONS

Written opinion of PCT/JP2018/023870 dated Sep. 25, 2018 and English Translation thereof.
(Continued)

*Primary Examiner* — Kevin F Murphy
(74) *Attorney, Agent, or Firm* — Muncy, Geissler, Olds & Lowe, P.C.

(57) ABSTRACT

[Problem]
To provide a check-valve in which the occurrence of damage such as tearing, deformation, etc., can be suppressed.
[Solution]
A check-valve opens and closes an opening provided in a main body and prevents a backflow of a fluid passing through the opening; and the check-valve includes a base part 71 which is flexible, and a valve part 72 which opens and closes the opening, has a thickness thinner than a thickness of the base part 71, and is connected to the base part 71 in a state in which a periphery of the valve part 72 is surrounded with the base part 71. The valve part 72 seals
(Continued)

the opening in a normal state of the valve part 72 being pre-urged toward the main body by an elasticity of the base part 71, and opens the opening when the fluid passes through the opening in one direction.

9 Claims, 5 Drawing Sheets (51) Int. Cl.
    *F16K 15/14*     (2006.01)
    *A61M 1/06*     (2006.01)

(52) U.S. Cl.
    CPC .......... *F16K 15/181* (2013.01); *F16K 15/185* (2013.01); *Y10T 137/7888* (2015.04); *Y10T 137/7891* (2015.04)

(56) References Cited

U.S. PATENT DOCUMENTS

| | | | | |
|---|---|---|---|---|
| 3,613,720 A * | 10/1971 | Welch | ............... | F16K 15/144 |
| | | | | 137/527.8 |
| 3,814,124 A * | 6/1974 | Bell | ............... | F16K 15/031 |
| | | | | 137/855 |
| 4,009,366 A * | 2/1977 | Danell | ............... | F02N 19/10 |
| | | | | 219/208 |
| 4,076,047 A * | 2/1978 | Akahori | ............... | F01L 3/205 |
| | | | | 137/856 |
| 5,364,244 A * | 11/1994 | Taylor-McCune | ............... | |
| | | | | F04B 53/1042 |
| | | | | 137/855 |
| 6,834,678 B2 * | 12/2004 | Santa | ............... | F16K 15/03 |
| | | | | 137/852 |
| 8,608,005 B2 * | 12/2013 | Streuer | ............... | H01M 2/1229 |
| | | | | 220/254.1 |
| 2004/0250863 A1 * | 12/2004 | Atkeson | ............... | F16K 25/005 |
| | | | | 137/855 |
| 2006/0169694 A1 | 8/2006 | Kemper | | |
| 2007/0179439 A1 | 8/2007 | Stefan | | |

FOREIGN PATENT DOCUMENTS

| | | |
|---|---|---|
| JP | S48-82526 U | 10/1973 |
| JP | S5515495 U | 1/1980 |
| JP | S6417073 U | 1/1989 |
| JP | H01-141318 U | 9/1989 |
| JP | H01148179 U | 10/1989 |
| JP | 2007-032451 A | 2/2007 |
| JP | 2012026515 A | 2/2012 |
| JP | 2014147496 A | 8/2014 |
| JP | 2015-152144 A | 8/2015 |

OTHER PUBLICATIONS

English Translation of International Search Report of PCT/JP2018/023870 dated Sep. 25, 2018.

\* cited by examiner

CHECK-VALVE

TECHNICAL FIELD

The invention relates to a check-valve preventing a backflow of a fluid passing through an opening.

BACKGROUND ART

A valve device discussed in Patent Literature 1 includes a tubular base part, and a valve body extending downward from a lower end of the base part and including, at a lower end of the valve body, a pair of planar movable parts which is closed by being normally-closed. In the valve device recited in Patent Literature 1, a slit-shaped cut is formed at a seam at the lower end of the pair of planar movable parts. For example, the valve device recited in Patent Literature 1 is called a duckbill valve, etc.

Generally, a duckbill valve such as the valve device recited in Patent Literature 1 or the like is formed as one body from a synthetic resin or the like. Then, after forming the entire valve device of the synthetic resin or the like, the slit-shaped cut is formed by cutting or incising the seam portion at the lower end of the pair of planar movable parts by using, for example, a cutter, a press, etc.

CITATION LIST

Patent Literature

[Patent Literature 1]
JP-A 2015-152144 (Kokai)

SUMMARY OF INVENTION

Problem to be Solved by the Invention

However, generally, the thickness of the lower end of the pair of planar movable parts is thinner than the thickness of the upper end of the pair of planar movable parts. Also, a relatively thin portion is exposed externally as the lower end part of the pair of planar movable parts. Therefore, there is room for improvement in that the relatively thin lower end part of the planar movable part of the valve device tears easily. Also, for example, the slit-shaped cut has a sharp configuration when the seam portion at the lower end of the pair of planar movable parts is cut or incised using a cutter, etc. Therefore, there is room for improvement in that the slit-shaped cut easily tears and/or deforms.

The invention is directed to solve these problems, and is directed to provide a check-valve in which the occurrence of damage such as tearing, deformation, etc., can be suppressed.

Means for Solving the Problem

According to the invention, these problems are solved by a check-valve which opens and closes an opening provided in a main body and prevents a backflow of a fluid passing through the opening; the check-valve includes a flexible base part, and a valve part which opens and closes the opening, has a thickness thinner than a thickness of the base part, and is connected to the base part in a state in which a periphery of the valve part is surrounded with the base part; and the valve part seals the opening in a normal state of the valve part being pre-urged toward the main body by an elasticity of the base part, and opens the opening when the fluid passes through the opening in one direction.

According to the configuration, the check-valve includes the flexible base part, and the valve part which opens and closes the opening provided in the main body. The valve part is connected to the base part in the state in which the periphery of the valve part is surrounded with the base part. Also, the thickness of the valve part is thinner than the thickness of the base part. Also, the valve part seals the opening in the normal state of the valve part being pre-urged toward the main body by the elasticity of the base part, and opens the opening when the fluid passes through the opening in the one direction. Thus, the periphery of the valve part which is thinner than the thickness of the base part is surrounded with the base part; therefore, the end part of the valve part is not exposed externally and is connected to the base part over the entire periphery. Tearing of the end part of the valve part can be suppressed thereby. Also, for example, a cut which is cut or incised by a cutter, etc., is not provided in the valve part; and the valve part seals the opening of the main body in the normal state of the valve part being pre-urged toward the main body by the elasticity of the base part. On the other hand, the valve part opens the opening when the fluid passes through the opening of the main body in one direction. Therefore, the valve part does not include a portion having a sharp configuration; and the fluid does not pass through the slit-shaped cut. The tearing and/or deformation of the valve part can be suppressed thereby. Thereby, the check-valve of the configuration can suppress the occurrence of damage such as tearing, deformation, etc.

Also, for example, a process of forming a cut which is cut or incised using a cutter, etc., is unnecessary. Therefore, the manufacturing processes of the check-valve can be simplified. Further, as described above, the periphery of the valve part which is thinner than the thickness of the base part is surrounded with the base part. In other words, the base part which is thicker than the thickness of the valve part surrounds the periphery of the valve part. Therefore, the excessive suctioning of the valve part via the opening toward the suction space of the main body can be suppressed. Therefore, a structure for preventing the excessive suctioning of the valve part toward the suction space of the main body is unnecessary around the opening. Thereby, the user easily can clean around the opening of the main body to which the check-valve is mounted.

Favorably, an interference amount between the valve part and the main body increases away from a portion where mounting to the main body is performed.

According to the configuration, the interference amount between the valve part and the main body is not always constant over the entire periphery. The interference amount between the valve part and the main body increases away from the portion where mounting to the main body is performed. Therefore, by adjusting the interference amount between the valve part and the main body, the valve part can be pre-urged toward the main body by the elasticity of the base part. Thereby, the valve part can seal the opening of the main body more reliably in the normal state.

Favorably, the valve part includes a circular bottom part and has a dome configuration protruding from the base part toward the opening.

According to the configuration, the valve part includes the circular bottom part and has the dome configuration protruding from the base part toward the opening of the main body. Therefore, a uniform force is applied to the valve part in the state in which the valve part seals the opening of the main body. In other words, in the state in which the valve part seals the opening of the main body, the force that the valve part receives from the main body is uniform over the entire contact portion between the valve part and the main body. Therefore, the occurrence of a gap between the valve part and the main body can be suppressed; and higher sealability can be ensured by the dome-shaped valve part being suctioned via the opening toward the suction space of the main body.

Favorably, a mounting part which is additionally provided at the base part and mounted to the main body is further included; and the mounting part includes a protrusion protruding outward from a side surface of the mounting part.

According to the configuration, the check-valve further includes the mounting part additionally provided at the base part. The mounting part corresponds to a portion mounted to the main body and includes the protrusion protruding outward from the side surface of the mounting part. Thereby, an operator that mounts the check-valve to the main body can use the operation sensation to discriminate that the check-valve is mounted reliably to the main body. Also, the detachment of the mounting part from the main body can be suppressed because the protrusion protrudes outward from the side surface of the mounting part.

Favorably, the mounting part further includes a built-up part having a material thickness built-up outward from the base part and the mounting part; and the built-up part is provided at a portion where the base part and the mounting part are connected to each other.

According to the configuration, the mounting part further includes the built-up part. The built-up part is provided at the portion where the base part and the mounting part are connected to each other. In the built-up part, the material thickness is built-up outward from the base part and the mounting part. Therefore, the interference portion between the main body and the portion where the base part and the mounting part are connected to each other can be ensured. Therefore, higher sealability or adhesion between the mounting part and the main body can be ensured.

Favorably, a grip part is further included, and is additionally provided at the base part at one side of the mounting part and extends in a reverse direction of an extension direction of the mounting part when viewed from the base part.

According to the configuration, the check-valve further includes the grip part. The grip part is additionally provided at the base part at one side of the mounting part. Also, the grip part extends in the reverse direction of the extension direction of the mounting part when viewed from the base part. Therefore, in the state in which the check-valve is mounted to the main body, the user easily can detach the check-valve from the main body by grasping and pulling the grip part. Thereby, the user easily can clean the check-valve and/or clean around the opening of the main body to which the check-valve is mounted.

Effects of the Invention

According to the invention, a check-valve can be provided in which the occurrence of damage such as tearing, deformation, etc., can be suppressed.

MODES FOR CARRYING OUT THE INVENTION

Favorable embodiments of the invention will now be described in detail with reference to the drawings.

Because the embodiments described below are favorable specific examples of the invention, various favorable technical limits are provided; but the scope of the invention is not limited to these aspects unless the invention is particularly and expressly limited in the following description. Also, similar components in the drawings are marked with the same reference numerals; and a detailed description is omitted as appropriate.

A check-valve according to the embodiment will now be described with reference to FIG. 1 and FIG. 2. The check-valve 7 according to the embodiment opens and closes an opening provided in a main body to which the check-valve 7 is mounted, and prevents a backflow of a fluid passing through the opening. For example, the main body of a breast pump used when a user expresses breast milk, the main body of a beverage server device supplying a beverage, etc., are examples of the main body. However, the main body to which the check-valve 7 is mounted is not limited thereto. Examples of the main body to which the check-valve 7 is mounted are described below with reference to FIG. 3 to FIG. 5.

Figure 1:
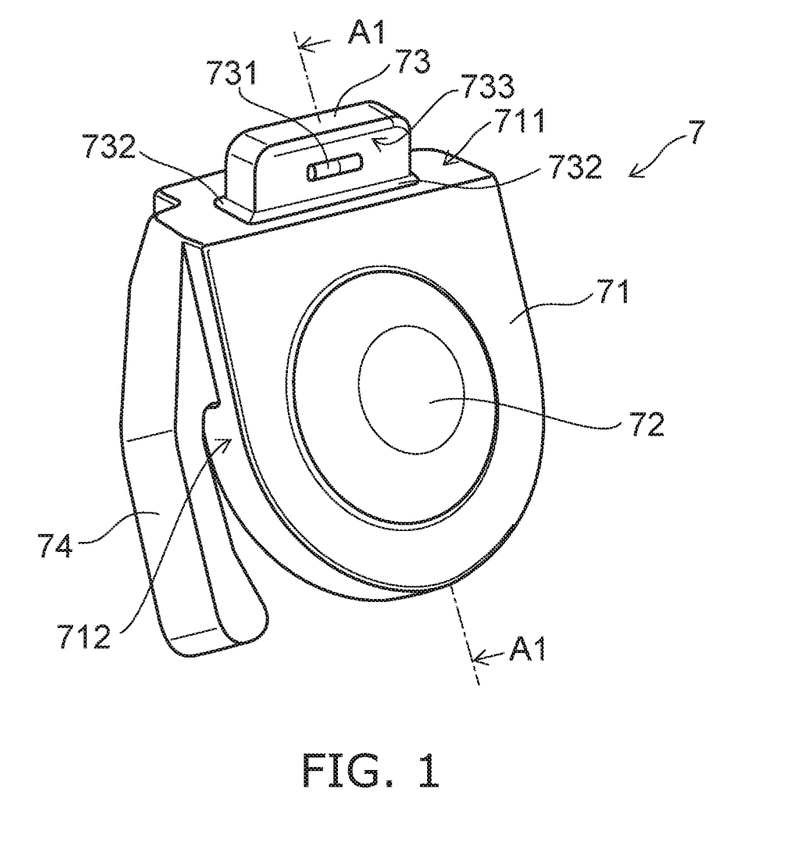
FIG. 1 is a perspective view illustrating a check-valve according to an embodiment of the invention.
Figure 2:
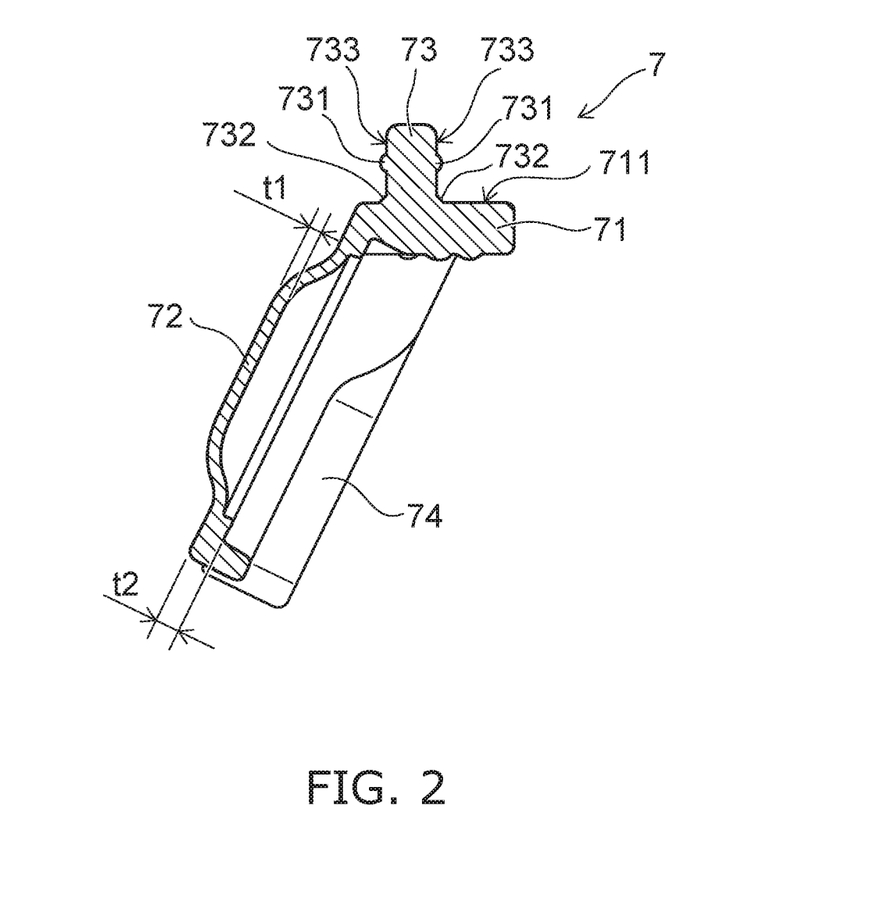
FIG. 2 is a cross-sectional view of an A1-A1 cross section illustrated in FIG. 1.

As illustrated in FIG. 1 and FIG. 2, the check-valve 7 according to the embodiment includes a base part 71, a valve part 72, a mounting part 73, and a grip part 74. The mounting part 73 and the grip part 74 may not always be provided. When the mounting part 73 is provided, the check-valve 7 is detachably provided on the main body. Also, when the grip part 74 is provided, the user easily can mount the check-valve 7 to the main body and can detach the check-valve 7 easily from the main body by grasping the grip part 74.

For example, the check-valve 7 is formed as one body from an elastic body of a synthetic resin, etc., and is flexible as an entirety. Therefore, the base part 71 and the valve part 72 are flexible. For example, silicone rubber, an elastomer, natural rubber or the like, etc., are examples of the material of the check-valve 7.

As illustrated in FIG. 1, the valve part 72 is connected to the base part 71 in a state in which the periphery of the valve part 72 is surrounded with the base part 71. Specifically, the valve part 72 includes a circular bottom part, and has a dome configuration protruding in a prescribed direction from the base part 71. The prescribed direction in which the valve part 72 protrudes is, for example, a direction toward the opening of the main body to which the check-valve 7 is mounted.

As illustrated in FIG. 2, a thickness t1 of the valve part 72 is thinner than a thickness t2 of the base part 71. Therefore, compared to the base part 71, the valve part 72 flexes easily and can seal the opening of the main body. Specifically, the valve part 72 is pre-urged toward the main body by the elasticity of the base part 71 and seals the opening of the main body in the normal state. The details are described below with reference to FIG. 3 to FIG. 5. On the other hand, the valve part 72 opens the opening of the main body when a fluid passes through the opening of the main body in one direction. Thus, the check-valve 7 according to the embodiment prevents the backflow of the fluid passing through the opening of the main body.

The mounting part 73 is additionally provided at the base part 71. In the check-valve 7 according to the embodiment, the mounting part 73 is provided at an upper surface 711 of the base part 71 and protrudes from the upper surface 711 of the base part 71. The mounting part 73 corresponds to the "portion where mounting to the main body is performed" when the check-valve 7 is mounted to the main body. The mounting part 73 includes a protrusion 731 protruding outward from a side surface 733. Therefore, the operator that mounts the check-valve 7 to the main body can use the operation sensation to discriminate that the check-valve 7 is mounted reliably to the main body. Also, the protrusion 731 can suppress the detachment of the mounting part 73 from the main body.

The mounting part 73 further includes a built-up part 732. The built-up part 732 is provided at the portion where the base part 71 and the mounting part 73 are connected to each other. Specifically, the built-up part 732 is provided over the upper surface 711 of the base part 71 and the side surface 733 of the mounting part 73. The built-up part 732 is a portion where the material thickness is built-up outward from the base part 71 and the mounting part 73. By providing the built-up part 732, the interference portion between the main body and the portion where the base part 71 and the mounting part 73 are connected to each other can be ensured. The details are described below with reference to FIG. 3 to FIG. 5.

The grip part 74 is additionally provided at the base part 71 at one side of the mounting part 73. In the check-valve 7 according to the embodiment, the grip part 74 is provided at a side surface 712 of the base part 71 at one side when viewed from the mounting part 73. When viewed from the base part 71, the grip part 74 extends in the reverse direction of the extension direction of the mounting part 73. In other words, in the check-valve 7 illustrated in FIG. 1, the mounting part 73 extends in the upward direction; and on the other hand, the grip part 74 extends in the downward direction. By providing the grip part 74, the user easily can mount the check-valve 7 to the main body and can detach check-valve 7 easily from the main body by grasping the grip part 74.

According to the check-valve 7 according to the embodiment, the periphery of the valve part 72 having the thickness t1 which is thinner than the thickness t2 of the base part 71 is surrounded with the base part 71. Therefore, the end part of the valve part 72 is not exposed externally and is connected to the base part 71 over the entire periphery. The tearing of the end part of the valve part 72 can be suppressed thereby. Also, for example, a cut which is cut or incised using a cutter, etc., is not provided in the valve part 72. The valve part 72 is pre-urged toward the main body by the elasticity of the base part 71 and seals the opening of the main body in the normal state. On the other hand, the valve part 72 opens the opening when the fluid passes through the opening of the main body in the one direction. Therefore, the valve part 72 does not include a portion having a sharp configuration; and the fluid does not pass through a slit-shaped cut. The tearing and/or deformation of the valve part 72 can be suppressed thereby. Thereby, the check-valve 7 according to the embodiment can suppress the occurrence of damage such as tearing, deformation, etc.

Also, for example, a process of forming a cut which is cut or incised using a cutter, etc., is unnecessary. Therefore, the manufacturing processes of the check-valve 7 can be simplified. Further, as described above, the periphery of the valve part having the thickness t1 which is thinner than the thickness t2 of the base part 71 is surrounded with the base part 71. In other words, the base part 71 which has the thickness t2 which is thicker than the thickness t1 of the valve part 72 surrounds the periphery of the valve part 72. Therefore, the excessive suctioning of the valve part 72 via the opening toward the suction space of the main body can be suppressed. Therefore, a structure (e.g., a rib structure and/or a mesh-shaped structure) for preventing the excessive suction of the valve part 72 toward the suction space of the main body is unnecessary around the opening of the main body. Thereby, the user easily can clean around the opening of the main body to which the check-valve 7 is mounted.

An example of the main body to which the check-valve 7 is mounted will now be described with reference to FIG. 3 to FIG. 5. As described above in reference to FIG. 1 and FIG. 2, for example, the check-valve 7 according to the embodiment is mounted to the main body of a breast pump used when a user expresses breast milk, the main body of a beverage server device supplying a beverage, etc. A case where the check-valve 7 is mounted to a main body 3 of a breast pump 2 is described as an example in FIG. 3 to FIG. 5.

Figure 3:
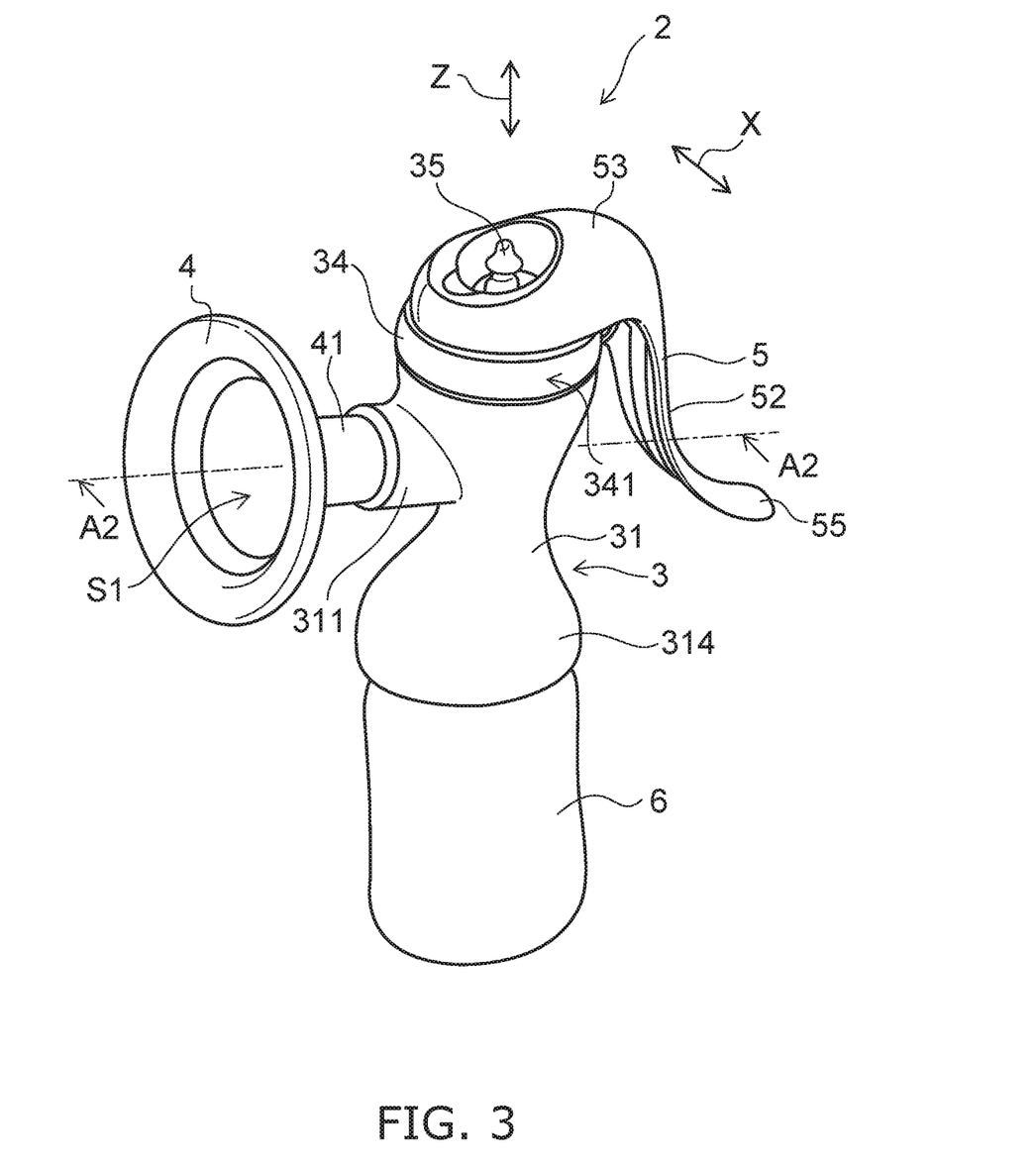
FIG. 3 is a perspective view illustrating a breast pump to which the check-valve according to the embodiment is mounted.
Figure 4:
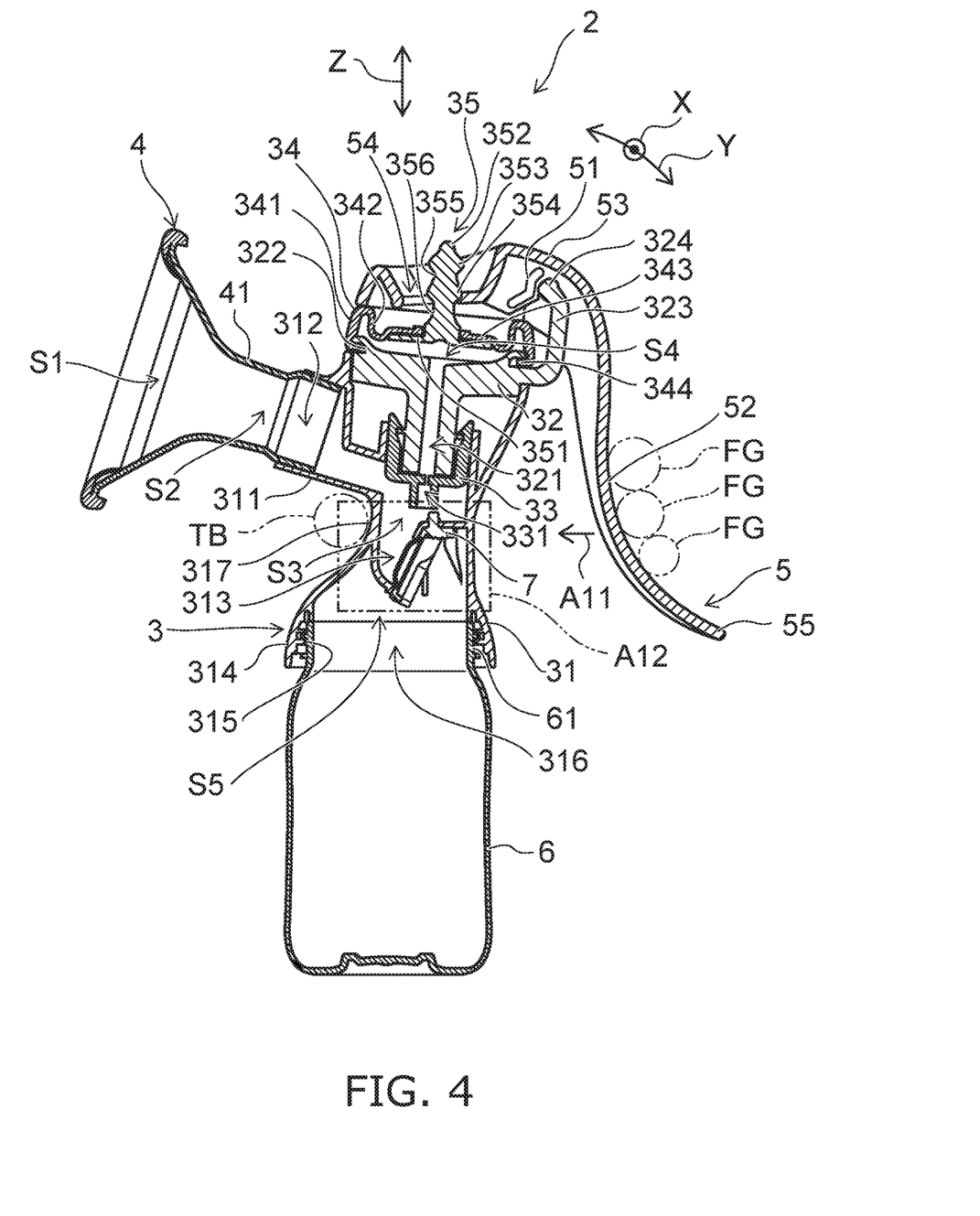
FIG. 4 is a cross-sectional view of an A2-A2 cross section illustrated in FIG. 3.
Figure 5:
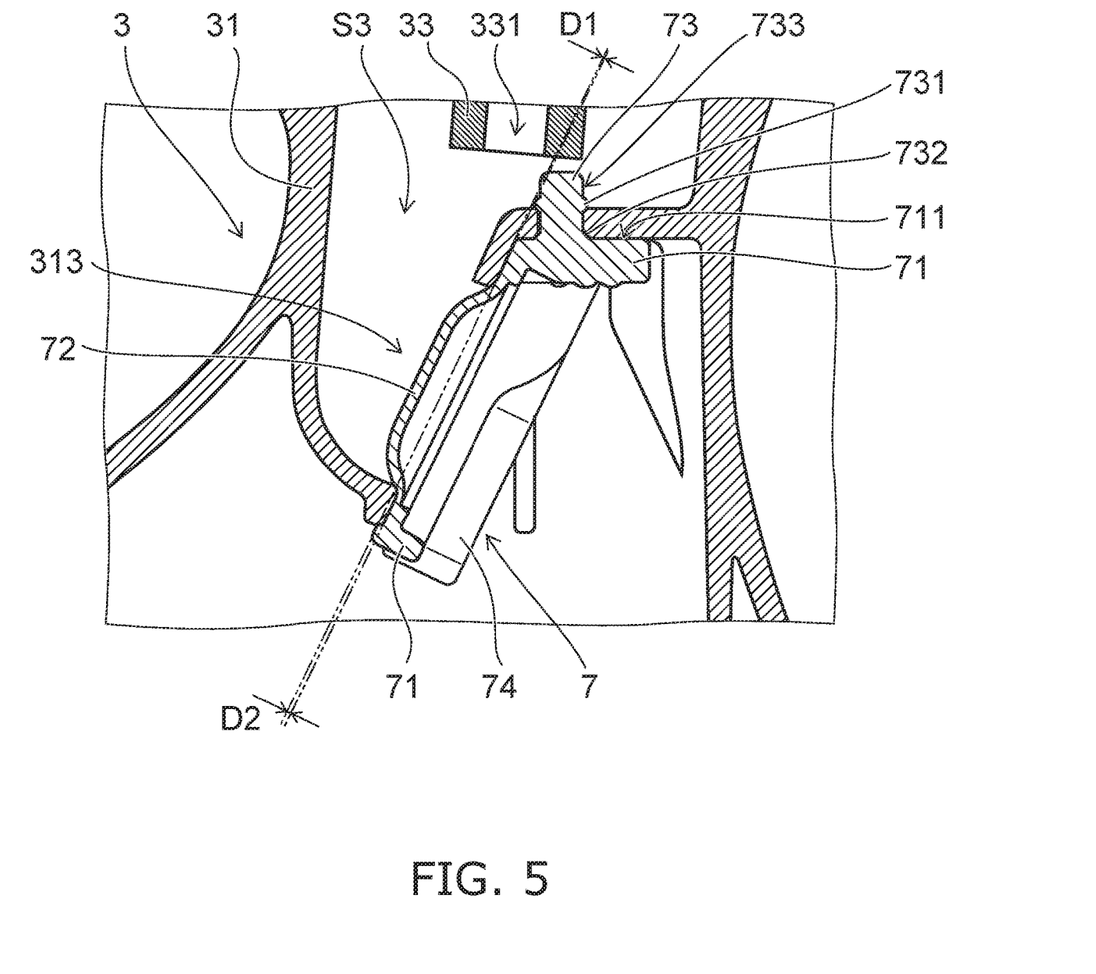
FIG. 5 is an enlarged view in which region A12 illustrated in FIG. 3 is enlarged.

The manual breast pump (for convenience of description in the description recited below, called simply the "breast pump") 2 illustrated in FIG. 3 to FIG. 5 is an implement which the user can manually operate to express breast milk, and which is used when it is difficult to give breast milk directly to an infant, when the nipple is injured, when preventing mastitis, etc. The user uses the breast pump 2 by holding the breast pump 2 in the user's own hand. Therefore, it is favorable for the breast pump 2 to be lightweight, to be operatable with one hand, and to be such that fatigue can be reduced.

The breast pump 2 includes the main body 3, a hood 4, a handle 5, and a bottle 6. The hood 4 is formed in a bugle-mouth configuration or a substantially dome configuration corresponding to the shape of a breast and is fitted to the breast. A reduced-diameter part 41 of the hood 4 where the diameter is smallest is connected to a mounting part 311 provided at the upper part of a casing 31 of the main body 3. When the user inserts the breast into a space S1 surrounded with the hood 4, the space S1 has a receiving space S2 which receives the nipple of the user to airtightly seal the nipple. A structure which can express breast milk is formed by setting the interior of the receiving space S2 to a negative pressure.

The main body 3 includes the casing 31, a base part 32, a base packing 33, a diaphragm 34, and a coupler 35. The check-valve 7 according to the embodiment is mounted in the interior of the casing 31 of the main body 3, opens and closes an opening 313 formed in the interior of the casing 31, and prevents the backflow of the breast milk passing through the opening 313.

The casing 31 is molded from a relatively light and hard synthetic resin material. For example, polypropylene, polycarbonate, polycycloolefin, polyethersulfone, polyphenylsulfone, etc., are examples of the material of the casing 31. The mounting part 311 to which the hood 4 is mounted has a first passageway 312 through which a gas, the expressed breast milk, etc., pass. As illustrated in FIG. 4, the first passageway 312 spatially communicates with a communicating part S4 via an inner space S3 formed in a substantially central part inside the casing 31, a through-hole 331 of the base packing 33, and a second passageway 321 formed in the interior of the base part 32.

The base part 32 is held by the casing 31 by means of the base packing 33. The base packing 33 is sandwiched between the casing 31 and the base part 32, holds the base part 32 to the casing 31, and prevents the breast milk from flowing through the gap between the casing 31 and the base part 32. In other words, the base packing 33 has a holding function of holding the base part 32 to the casing 31, and a backflow prevention function of preventing the breast milk from flowing through the gap between the casing 31 and the base part 32.

The diaphragm 34 is provided at the upper part of the base part 32. For example, the diaphragm 34 is formed as one body from an elastic body of a synthetic resin, etc., and is flexible as an entirety. The diaphragm 34 is stretched to catch on the upper part of the base part 32 and to be connected to the upper part of the base part 32. Specifically, the diaphragm 34 is mounted to the base part 32 by a lower end part 344 of the diaphragm 34 catching on a groove part 322 provided in the upper part of the base part 32.

The base part 32 includes an arm 323 provided at a position on the side opposite to the mounting part 311. The arm 323 extends to a position higher than the position where the diaphragm 34 is connected to the base part 32. Favorably, the arm 323 extends to the position higher than the upper end of the diaphragm 34 at a position adjacent to the diaphragm 34. A spindle part 324 which rotatably supports the handle 5 is formed at the upper end part of the arm 323. The spindle part 324 extends from the arm 323 along a width direction X of the handle 5 and is connected detachably at two end parts to a pair of bearing parts 51 provided at the inner side of the handle 5. Thereby, the handle 5 can rotate around the spindle part 324 (a Y-direction illustrated in FIG. 4) with the spindle part 324 of the base part 32 as the center. In other words, the casing 31 has a size which the user can grip with one hand. At the outer perimeter side surface at the hood 4 side as illustrated in FIG. 4, the casing 31 has a curved recess 317 to which a thumb TB can closely contact easily. In a state in which the thumb TB is placed on the recess 317, the user can touch any finger FG other than the thumb to a lever part 52 of the handle 5 and can simultaneously grip the casing 31 and the lever part 52 with one hand. Then, the user can perform the rotation operation of the handle 5 with the spindle part 324 as the center by clenching and relaxing the hand gripping the casing 31 and the lever part 52. The pivotally-supporting structure of the handle 5 is not limited thereto. For example, the bearing parts 51 of the handle 5 may be circular through-holes. In such a case, the spindle part 324 of the arm 323 passes through the bearing parts 51 which are through-holes.

The communicating part S4 which is formed between the base part 32 and the diaphragm 34 is a region (a space) where the negative pressure is applied. The structure of the base part 32 is not limited to the structure illustrated in FIG. 4 as long as the base part 32 is connected to the diaphragm 34 and can cover and seal the communicating part S4. For example, the base part may be formed as a circular tubular or cup-shaped member including a wall part which has sufficient height to surround the periphery of the space where the negative pressure of the communicating part S4 is applied. When the communicating part S4 formed between the base part 32 and the diaphragm 34 is set to a negative-pressure state due to the diaphragm 34 changing, the space S1 which is surrounded with the hood 4 is set to a negative-pressure state via the second passageway 321 of the base part 32, the through-hole 331 of the base packing 33, the inner space S3 of the casing 31, and the first passageway 312.

The lower side of the inner space S3 of the casing 31 is open toward the bottle 6 via the opening 313. As illustrated in FIG. 5, the check-valve 7 according to the embodiment is mounted to the casing 31 by the mounting part 73 at the portion where the opening 313 is formed. As described above in reference to FIG. 1 and FIG. 2, the mounting part 73 includes the protrusion 731 protruding outward from the side surface 733. Therefore, when the check-valve 7 is mounted to the casing 31 as illustrated in FIG. 5, the operator can use the operation sensation (e.g., a click sensation or the like) to discriminate that the check-valve 7 is mounted reliably to the casing 31. Also, the detachment of the mounting part 73 from the casing 31 can be suppressed because the protrusion 731 protrudes outward from the side surface 733 of the mounting part 73.

Also, as described above in reference to FIG. 1 and FIG. 2, the mounting part 73 further includes the built-up part 732. Therefore, as illustrated in FIG. 5, the interference portion between the casing 31 and the portion where the base part 71 and the mounting part 73 are connected to each other (the portion where the built-up part 732 is provided) can be ensured. In other words, the built-up part 732 can jut into the casing 31 of the main body 3. Therefore, higher sealability or adhesion between the mounting part 73 and the casing 31 can be ensured.

The valve part 72 of the check-valve 7 is pre-urged toward the casing 31 of the main body 3 by the elasticity of the base part 71 and seals the opening 313 in the normal state (normally-closed). In other words, in the state of being mounted to the casing 31, the check-valve 7 is pressed toward the casing 31 by the elasticity of the base part 71 and virtually includes a portion (an overlapping portion) interfering with the casing 31. That is, a bias in a direction toward the casing 31 is applied to the check-valve 7 by the elasticity of the base part 71. As illustrated in FIG. 5, the interference amount between the valve part 72 of the check-valve 7 and the casing 31 of the main body 3 is not always constant over the entire periphery of the valve part 72 and increases away from the portion (the mounting part 73) where the check-valve 7 is mounted to the casing 31. Specifically, in the state in which the check-valve 7 is mounted to the casing 31, an interference amount D2 between the casing 31 and the valve part 72 at a relatively distal position when viewed from the mounting part 73 is larger than an interference amount D1 between the casing 31 and the valve part 72 at a relatively proximal position when viewed from the mounting part 73. That is, the angle between the surface of the casing 31 contacting the upper surface 711 of the base part 71 and the portion of the casing 31 contacting the valve part 72 (the peripheral portion of the opening 313) is smaller than the angle between the upper surface 711 of the base part 71 and the portion of the valve part 72 contacting the casing 31 (the peripheral portion of the valve part 72). Thus, the valve part 72 can be pre-urged toward the casing 31 by the elasticity of the base part 71 by adjusting the interference amount between the valve part 72 and the casing 31. Thereby, the valve part 72 can be pre-urged toward the casing 31 of the main body 3 by the elasticity of the base part 71 and can more reliably seal the opening 313 in the normal state.

When the communicating part S4 is set to a negative-pressure state, the inner space S3 of the casing 31 is set to a negative-pressure state via the second passageway 321 of the base part 32 and the through-hole 331 of the base packing 33. Then, the valve part 72 of the check-valve 7 is suctioned toward the inner space (the suction space) S3 via the opening 313 of the casing 31. Here, the valve part 72 includes a circular bottom part and has a dome configuration protruding toward the opening 313 from the base part 71. In other words, the distance between the center of the valve part 72 and the portion of the valve part 72 contacting the casing 31 (the peripheral portion of the valve part 72) is substantially the same over the entire periphery of the valve part 72. Therefore, a uniform force is applied to the valve part 72 in the state in which the valve part 72 seals the opening 313. In other words, in the state in which the valve part 72 seals the opening 313, the force on the valve part 72 from the casing 31 is uniform over the entire contact portion between the valve part 72 and the casing 31. Therefore, the occurrence of the gap between the valve part 72 and the casing 31 can be suppressed; and the dome-shaped valve part 72 can ensure higher sealability by being suctioned toward the inner space S3 via the opening 313.

At this time, as described above in reference to FIG. 1 and FIG. 2, the excessive suction of the valve part 72 toward the inner space S3 via the opening 313 is suppressed. Therefore, a structure (e.g., a rib structure, a mesh-shaped structure, etc.) for preventing the excessive suction of the valve part 72 toward the inner space S3 is unnecessary around the opening 313. Thereby, the user easily can clean around the opening 313 where the check-valve 7 is mounted. Also, as described above in reference to FIG. 1 and FIG. 2, the check-valve 7 includes the grip part 74. Therefore, the user easily can detach the check-valve 7 from the main body 3 by grasping the grip part 74. Thereby, the user even more easily can clean around the opening 313 where the check-valve 7 is mounted.

When the negative-pressure state of the communicating part S4 is released and a prescribed amount of the expressed breast milk is collected at the region (the inner space S3) of the valve part 72 and the opening 313, the valve part 72 of the check-valve 7 opens the opening 313 due to the weight of the breast milk and/or the release of the negative pressure (the change of the pressure). Thereby, the expressed breast milk is guided into the interior of the bottle 6 via the opening 313.

The casing 31 includes, at the lower end part of the casing 31, a detachable part 314 which is provided detachably on the bottle 6. The detachable part 314 has a dome configuration or a tubular configuration and has a space S5 communicating with the inner space S3 when the check-valve 7 opens the opening 313. An internal-thread part 315 is provided at the inner side of the detachable part 314. On the other hand, an external-thread part 61 is provided at the outer side of the upper end part of the bottle 6. The internal-thread part 315 of the detachable part 314 and the external-thread part 61 of the bottle 6 can screw together. The bottle 6 may be an exclusive part of the breast pump 2 or may be a nursing bottle suited to the detachable part 314, etc. Also, the bottle 6 may not be a molded container, and may have a bag configuration. The end part of the detachable part 314 of the embodiment has an opening 316 which corresponds to the bottle opening of any nursing bottle so that not only the bottle 6 which is an exclusive part of the breast pump 2 but also any nursing bottle can be attached and detached.

The diaphragm 34 is a negative-pressure generation member for generating a negative pressure. In the embodiment, the diaphragm 34 is connected to the upper part of the base part 32 and covers the communicating part S4. As illustrated in FIG. 4, the diaphragm 34 is bent complexly and has a sheet configuration resembling a relatively flat-bottomed circular tubular body as an entirety. Specifically, the diaphragm 34 includes a first wall part 341 which is upright at the outer side, and a second wall part 342 as an inner wall part where the upper end part is folded back inward as one body. The first wall part 341 has enough rigidity to maintain the outer diameter. The thickness of the second wall part 342 is thinner than the thickness of the first wall part 341. The second wall part 342 is provided as a deforming part. A bottom surface part 343 is connected to the lower end of the second wall part 342. The bottom surface part 343 is formed as one body with the second wall part 342 as a relatively wide inner bottom part and extends from the second wall part 342 toward the center to seal the circular tubular lower part. In other words, the first wall part 341 and the second wall part 342 are formed of the same material. Also, the first wall part 341 and the second wall part 342 are provided with mutually-different rigidities by setting the thicknesses of the material to be different from each other. Therefore, when the external force due to the operation of the handle 5 acts on the diaphragm 34, the second wall part 342 can deform even when the external force that acts is of a level at which the first wall part 341 would not deform.

The diaphragm 34 is formed of a relatively highly elastic flexible deforming material, i.e., a synthetic resin having a hardness of about HS 30 to 70 using a type-A durometer of JIS-K6253 (ISO 7619). For example, silicone rubber, isoprene rubber, an elastomer such as SEBS (styrene-ethylene-butylene-styrene) or the like, etc., are examples of the material of the diaphragm 34. In the embodiment, silicone rubber is utilized as the material of the diaphragm 34. Favorably, the thickness of the material of the portion of the first wall part 341 is, for example, not less than about 1.5 mm and not more than about 3.0 mm. Specifically, the first wall part 341 of the diaphragm 34 extends downward and includes the lower end part 344 folded inward at the lower end. Similarly to the portion of the first wall part 341, the thickness of the lower end part 344 is, for example, not less than about 1.5 mm and not more than about 3.0 mm.

When the diaphragm 34 receives the action of the operation of the handle 5, the second wall part 342 deforms as the deforming part. Then, the volume of the space of the communicating part S4 formed between the bottom surface part 343 and the base part 32 changes. Thereby, the diaphragm 34 provides a constant amount of negative pressure to the communicating part S4. That is, the communicating part S4 changes to a negative-pressure state due to the deformation of the diaphragm 34. When the communicating part S4 changes to the negative-pressure state, the air inside the first passageway 312 is suctioned via the second passageway 321, the through-hole 331, and the inner space S3; and the breast milk is suctioned (expressed). At this time, the first wall part 341 substantially does not deform; and the connection state to the base part 32 is maintained.

The diaphragm 34 of the embodiment includes the upright first wall part 341. Therefore, even if the height of the base part 32 is not very high, the diaphragm. 34 can deform sufficiently above the base part 32 and can generate the necessary negative pressure in the communicating part S4. However, the configuration of the diaphragm 34 is not limited thereto. For example, when the base part is provided as a circular tubular or cup-shaped member including a wall part which has sufficient height to surround the periphery of the communicating part S4, the diaphragm may have a configuration which covers and is connected to the opening at the upper side of the circular tubular or cup-shaped base part and is recessed toward the inner side of the circular tubular or cup-shaped base part. In such a case, the diaphragm can deform inside the circular tubular or cup-shaped base part. Also, the diaphragm 34 is not limited to a detachable type and may be fixed to the base part 32.

The coupler 35 is provided in the diaphragm 34, is linked to the handle 5, and deforms the second wall part 342 of the diaphragm 34. The coupler 35 is formed of a hard material that is harder than the material of the second wall part 342 used as the deforming part. For example, synthetic resins such as polypropylene, polycarbonate, polycycloolefin, polyethersulfone, etc., are examples of the material of the coupler 35. The coupler 35 includes a flat disk-shaped base part 351. The base part 351 is disposed at the lower side (the communicating part S4 side) of the bottom surface part 343.

Also, the coupler 35 includes a linking part 352 protruding upward from the base part 351 and extending in an axis configuration. The linking part 352 is linked to the handle 5. Specifically, the linking part 352 is linkable to the handle 5 by being inserted through a through-hole (a hole having a smaller diameter than the base part 351) formed in the central part of the bottom surface part 343 of the diaphragm 34 and by being exposed at the upper side of the bottom surface part 343. The base part 351 pushes the bottom surface part 343 of the diaphragm 34 upward when the user pulls the handle 5 linked to the linking part 352 upward. Then, the second wall part 342 of the diaphragm 34 greatly deforms the space of the communicating part S4. The base part 351 of the embodiment is disposed at the lower side of the bottom surface part 343 of the diaphragm 34 without being connected to the bottom surface part 343. However, the mounting form of the base part 351 is not limited thereto. For example, the base part 351 may be fixed at the upper side of the bottom surface part 343.

The linking part 352 includes a first protruding part 353 and a second protruding part 354 which are disposed to be arranged with each other in an extension direction Z of the linking part 352 (referring to FIG. 3 and FIG. 4). The first protruding part 353 and the second protruding part 354 each protrude in a diametrically outward direction from the axial part of the linking part 352. A first engager 355 is provided between the first protruding part 353 and the second protruding part 354. The first engager 355 is a recessed portion (a groove portion) between the first protruding part 353 and the second protruding part 354. Also, a second engager 356 is provided between the second protruding part 354 and the base part 351. The second engager 356 is a recessed portion (a groove portion) between the second protruding part 354 and the base part 351.

The handle 5 is linked to the linking part 352 by engaging the first engager 355 or the second engager 356. The link position in the extension direction Z between the handle 5 and the linking part 352 is modifiable thereby. Therefore, the distance that the handle 5 pulls the linking part 352 upward is modifiable. The deformation amount of the diaphragm 34 can be modified thereby. In other words, as illustrated in FIG. 4, the first engager 355 and the second engager 356 are formed in stages to be separated from each other in the extension direction Z. Therefore, the distance that the handle 5 pulls the linking part 352 upward is modifiable in stages according to the engagement position between the handle 5 and the engagers 355 and 356.

The handle 5 has a long configuration and is molded as an entirety from a relatively hard and lightweight synthetic resin. For example, polypropylene, polycarbonate, polycycloolefin, polyethersulfone, etc., are examples of the material of the handle 5. The handle 5 includes a lift part 53 which is disposed above the diaphragm 34 and lifts the diaphragm 34 upward, and a lever part 52 which is bent from the lift part 53 and positioned at the side surface of the main body 3.

A linked part 54 which is linked to the linking part 352 is provided in the lift part 53. The linked part 54 has a retaining opening for retaining the link position of the linking part 352, and an insertion opening for inserting the linking part 352. The retaining opening and the insertion opening are connected spatially to each other. The inner diameter of the retaining opening is slightly larger than each of the outer diameters of the first engager 355 and the second engager 356, but is smaller than each of the outer diameters of the first protruding part 353 and the second protruding part 354. Conversely, the inner diameter of the insertion opening is larger than each of the outer diameters of the first protruding part 353 and the second protruding part 354. Thereby, the user can align the handle 5 and the linking part 352 to each other by inserting the linking part 352 into the insertion opening and subsequently sliding the linking part 352 toward the retaining opening to insert the first engager 355 or the second engager 356 into the retaining opening.

The lever part 52 is formed in a lever configuration and performs the role of a hand hold. The outer region of the lever part 52 corresponds to a region where the user places the fingers FG other than the thumb. That is, the outer surface of the lever part 52 corresponds to a surface that the user touches with the fingers FG other than the thumb. The distance between the outer surface of the lever part 52 to which the user touches the fingers FG and the recess 317 where the user places the thumb TB is a distance such that the user can grip by squeezing the casing 31 of the main body 3 between the recess 317 and the outer surface of the lever part 52. By the user clenching the hand which grips the casing 31 by squeezing, the lever part 52 is pressed in the direction of arrow A11 illustrated in FIG. 4 and approaches the main body 3. Then, the handle 5 rotates with the spindle part 324 as the center. Then, the lift part 53 of the handle 5 lifts the diaphragm 34 upward by means of the coupler 35. Then, the volume of the space of the communicating part S4 enlarges and changes to a negative-pressure state. Thereby, the receiving space S2 and the space S1 which are surrounded with the hood 4 change to a negative-pressure state via the second passageway 321 of the base part 32, the through-hole 331 of the base packing 33, the inner space S3 of the casing 31, and the first passageway 312. Thus, the expression of the breast milk is performed.

Downward from the region where the fingers FG are placed, the lever part 52 gradually curves outward. The appearance of a lower end part 55 of the handle 5 is slightly curled outward thereby. Therefore, the fingers FG can be suppressed from slipping toward the lower side of the handle 5 when the user causes the lever part 52 to approach the main body 3.

Hereinabove, embodiments of the invention are described. However, the invention is not limited to the embodiments recited above; and various modifications can be performed without departing from the scope of the claims. The configurations of the embodiments recited above can be partially omitted; and arbitrary combinations different from those recited above are possible.

REFERENCE NUMERAL LIST 2 breast pump
3 main body
4 hood
5 handle 6 bottle
7 check-valve
31 casing
32 base part
33 base packing
34 diaphragm
35 coupler
41 reduced-diameter part
51 bearing part
52 lever part
53 lift part
54 linked part
55 lower end part
61 external-thread part
71 base part
72 valve part
73 mounting part
74 grip part
311 mounting part
312 first passageway
313 opening
314 detachable part
315 internal-thread part
316 opening
317 recess
321 second passageway
322 groove part
323 arm
324 spindle part
331 through-hole
341 first wall part
342 second wall part
343 bottom surface part
344 lower end part
351 base part
352 linking part
353 first protruding part
354 second protruding part
355 first engager
356 second engager
711 upper surface
712 side surface
731 protrusion
732 built-up part
733 side surface
D1, D2 interference amounts
FG finger
S1 space
S2 receiving space
S3 inner space
S4 communicating part
S5 space
TB thumb

The invention claimed is:

1. A check-valve which opens and closes an opening provided in a main body and prevents a backflow of a fluid passing through the opening, the check-valve comprising:
a base part which is flexible; and
a valve part which opens and closes the opening, has a thickness thinner than a thickness of the base part, and is connected to the base part in a state in which a periphery of the valve part is surrounded with the base part, the periphery of the valve part being entirely connected to the base part, wherein
the valve part, which does not have any slit such that the fluid never passes through the valve part, seals the opening in a normal state of the valve part being pre-urged toward the main body by an elasticity of the base part, and the valve part opens the opening when the fluid passes through the opening in one direction, and
the valve part includes a bottom part and has a dome configuration protruding from the base part toward the opening, and the bottom part is circular.

2. The check-valve according to claim 1, further comprising a mounting part additionally provided at the base part and mounted to the main body, wherein
the mounting part includes a protrusion protruding outward from a side surface of the mounting part.

3. The check-valve according to claim 2, wherein the mounting part further includes a built-up part having a material thickness built-up outward from the base part and the mounting part, and the built-up part is provided at a portion where the base part and the mounting part are connected to each other.

4. The check-valve according to claim 2, further comprising a grip part which is additionally provided at the base part at one side of the mounting part and extends in a reverse direction of an extension direction of the mounting part when viewed from the base part.

5. The check-valve according to claim 1, further comprising:
a mounting part, wherein
the valve part, the base part and the mounting part are integrally formed of a single elastic material and the valve part and the base part are attached to the main body though the mounting part,
the valve part and the base part are configured to pivot around the mounting part such that the valve part pivots between a close position and an open position, the close position being taken at the normal state,
the peripheral of the valve part is larger than a peripheral of the opening such that the valve part entirely covers the opening when being at the close position such that fluid is prevented from passing through the valve part.

6. The check-valve according to claim 5, wherein
a shape of the peripheral of the valve part is similar to a shape of the peripheral of the opening.

7. The check-valve according to claim 6, wherein
the thickness of the valve part is uniform.

8. A check-valve which opens and closes an opening provided in a main body and prevents a backflow of a fluid passing through the opening, the check-valve comprising:
a base part which is flexible; and
a valve part which opens and closes the opening, has a thickness thinner than a thickness of the base part, and is connected to the base part in a state in which a periphery of the valve part is surrounded with the base part, the periphery of the valve part being entirely connected to the base part, wherein
the valve, which does not have any slit such that the fluid never passes through the valve part, seals the opening in a normal state of the valve part being pre-urged toward the main body by an elasticity of the base part, and the valve part opens the opening when the fluid passes through the opening in one direction, and
a deformed amount of the base part, which is caused by being pressed toward the main body with the elasticity of the base part, increases away from a portion where mounting to the main body is performed.

9. A breast pump for sucking breast milk, comprising:
a hood that sucks the breast milk from a user, a bottle that contains breast milk sucked from the user and delivered from the hood through a passage that connects the hood to the bottle, and a check-valve which opens and closes an opening provided in a main body and prevents a backflow of a fluid passing through the opening, the check-valve comprising:

a base part which is flexible;

a valve part which opens and closes the opening, has a thickness thinner than a thickness of the base part, and is connected to the base part in a state in which a periphery of the valve part is surrounded with the base part, the periphery of the valve part being entirely connected to the base part, and a mounting part, wherein the valve part, which does not have any slit such that the fluid never passes through the valve part, seals the opening in a normal state of the valve part being pre-urge toward the main body by an elasticity of the base part, and the valve part opens the opening when the fluid passes through the opening in one direction, the valve part, the base part and the mounting part are integrally formed of a single elastic material and the valve part and the base part are attached to the main body though the mounting part, the valve part and the base part are configured to pivot around the mounting part such that the valve part pivots between a close position and an open position, the close position being taken at the normal state, and the peripheral of the valve part is larger than a peripheral of the opening such that the valve part entirely covers the opening when being at the close position such that fluid is prevented from passing through the valve part, the check-valve is installed in the passage such that the sucked breast milk, which is the fluid, reaches the bottle passing through the check-valve, the valve part is formed in a dome configuration, seen from a cross-sectional view, and a protrusion of the dome configuration is positioned inside the passage and oriented toward the hood, and the base part is connected to the valve part on a side facing the bottle such that the one direction in which the breast milk passes through the opening is determined from the hood to the bottle.

* * * * *